United States Patent
Beaudet

(10) Patent No.: US 9,913,681 B2
(45) Date of Patent: Mar. 13, 2018

(54) ABLATION DEVICE USING BIPOLAR STEAM GENERATION

(71) Applicant: HOLOGIC, INC., Bedford, MA (US)

(72) Inventor: Daniel A. Beaudet, Lexington, MA (US)

(73) Assignee: HOLOGIC, INC., Marlborough, MA (US)

( * ) Notice: Subject to any disclaimer, the term of this patent is extended or adjusted under 35 U.S.C. 154(b) by 144 days.

(21) Appl. No.: 14/428,448

(22) PCT Filed: Sep. 19, 2013

(86) PCT No.: PCT/US2013/060613
§ 371 (c)(1),
(2) Date: Mar. 16, 2015

(87) PCT Pub. No.: WO2014/047282
PCT Pub. Date: Mar. 27, 2014

(65) Prior Publication Data
US 2015/0223876 A1    Aug. 13, 2015

Related U.S. Application Data

(60) Provisional application No. 61/702,926, filed on Sep. 19, 2012.

(51) Int. Cl.
*A61B 18/12* (2006.01)
*A61B 18/14* (2006.01)
*A61B 18/00* (2006.01)

(52) U.S. Cl.
CPC ...... *A61B 18/1485* (2013.01); *A61B 18/1233* (2013.01); *A61B 2018/00065* (2013.01); *A61B 2018/00154* (2013.01); *A61B 2018/00559* (2013.01); *A61B 2018/00577* (2013.01); *A61B 2018/00702* (2013.01);
(Continued)

(58) Field of Classification Search
CPC ............ A61B 18/1233; A61B 18/1485; A61B 2018/00065; A61B 2018/00154; A61B 2018/00559; A61B 2018/00577; A61B 2018/00702; A61B 2018/00875;
(Continued)

(56) References Cited

U.S. PATENT DOCUMENTS 5,562,720 A * 10/1996 Stern .................. A61B 18/1206
606/32
5,575,788 A * 11/1996 Baker ................ A61B 18/1485
606/192

(Continued)

OTHER PUBLICATIONS

PCT Notification of Transmittal of the International Search Report and the Written Opinion of the International Searching Authority for PCT/US2013/060613, filed Sep. 19, 2013, Applicant Hologic, Inc., dated Dec. 12, 2013, (10 pages).

*Primary Examiner* — Daniel Fowler
(74) *Attorney, Agent, or Firm* — Vista IP Law Group LLP

(57) ABSTRACT

An ablation device includes first and second electrodes and an absorbent medium. The ablation device may include a permeable spacer or other mechanisms to position the ablation device in the uterus. The absorbent medium configured to absorb a conductive fluid and optionally to distend. A current can be applied to the first and second electrodes to convert the conductive fluid to a vapor or steam for ablation of the uterus.

10 Claims, 7 Drawing Sheets

(52) U.S. Cl.
CPC .............. *A61B 2018/00875* (2013.01); *A61B 2018/1405* (2013.01); *A61B 2018/1472* (2013.01); *A61B 2018/1497* (2013.01); *A61B 2217/005* (2013.01)

(58) Field of Classification Search
CPC .... A61B 2018/1405; A61B 2018/1472; A61B 2018/1497; A61B 2217/005
See application file for complete search history.

(56) References Cited

U.S. PATENT DOCUMENTS

| | | | | |
|---|---|---|---|---|
| 5,683,366 | A * | 11/1997 | Eggers | A61B 18/12 604/114 |
| 5,891,094 | A | 4/1999 | Masterson et al. | |
| 6,091,993 | A * | 7/2000 | Bouchier | A61B 18/1485 606/32 |
| 6,159,207 | A | 12/2000 | Yoon | |
| 6,475,214 | B1 * | 11/2002 | Moaddeb | A61B 18/1492 606/41 |
| 6,669,694 | B2 | 12/2003 | Shadduck | |
| 2001/0032001 | A1 * | 10/2001 | Ricart | A61B 18/1402 607/99 |
| 2002/0068934 | A1 * | 6/2002 | Edwards | A61B 18/1477 606/41 |
| 2004/0230281 | A1 * | 11/2004 | Heil | A61B 17/320068 607/126 |
| 2010/0228239 | A1 | 9/2010 | Freed | |
| 2012/0065632 | A1 | 3/2012 | Shadduck | |

* cited by examiner

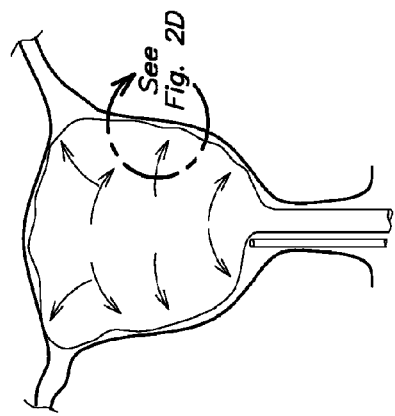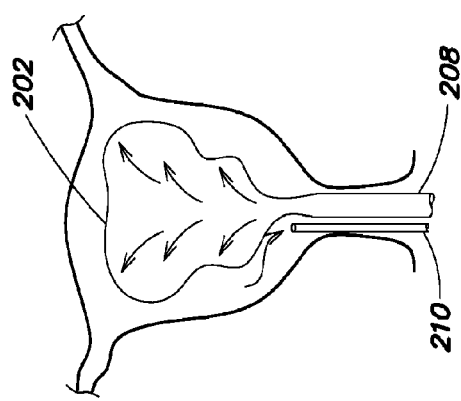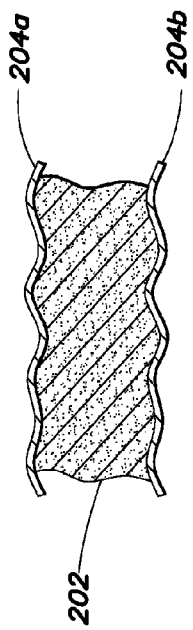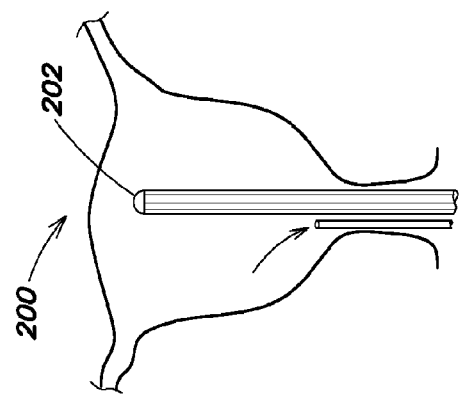
FIG. 2C
FIG. 2B
FIG. 2D
FIG. 2A

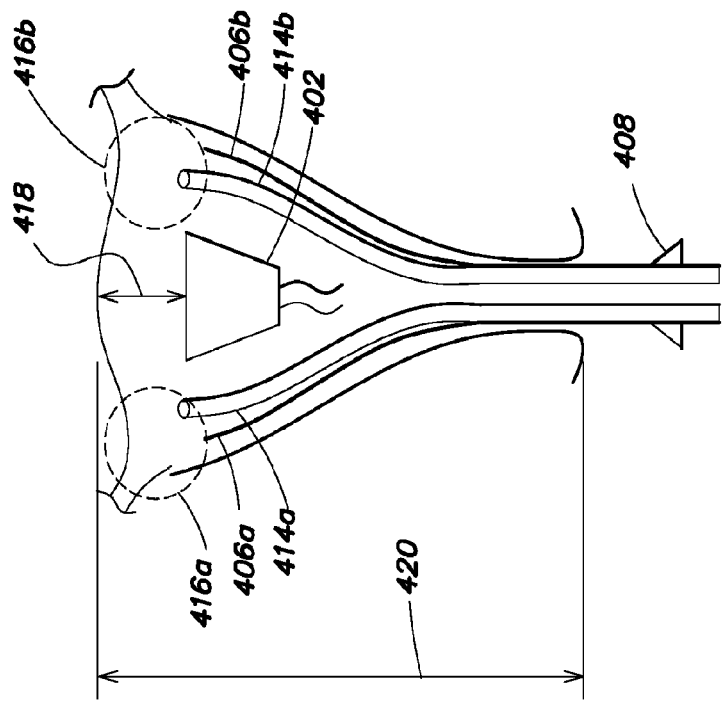
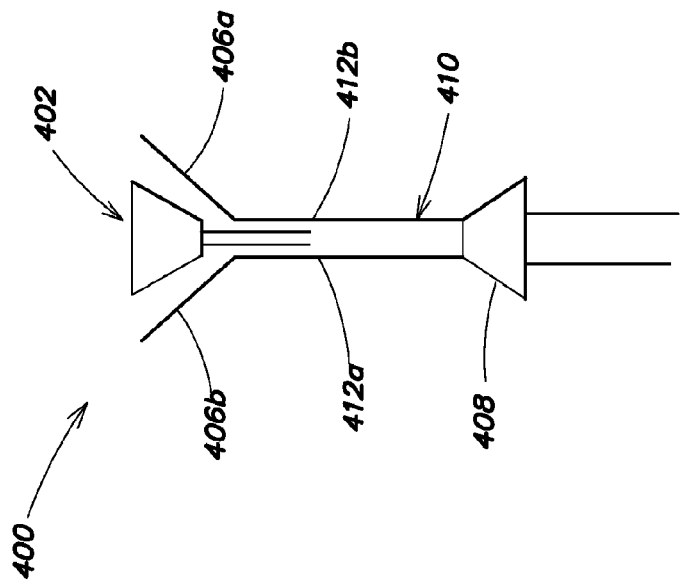
FIG. 4B
FIG. 4A

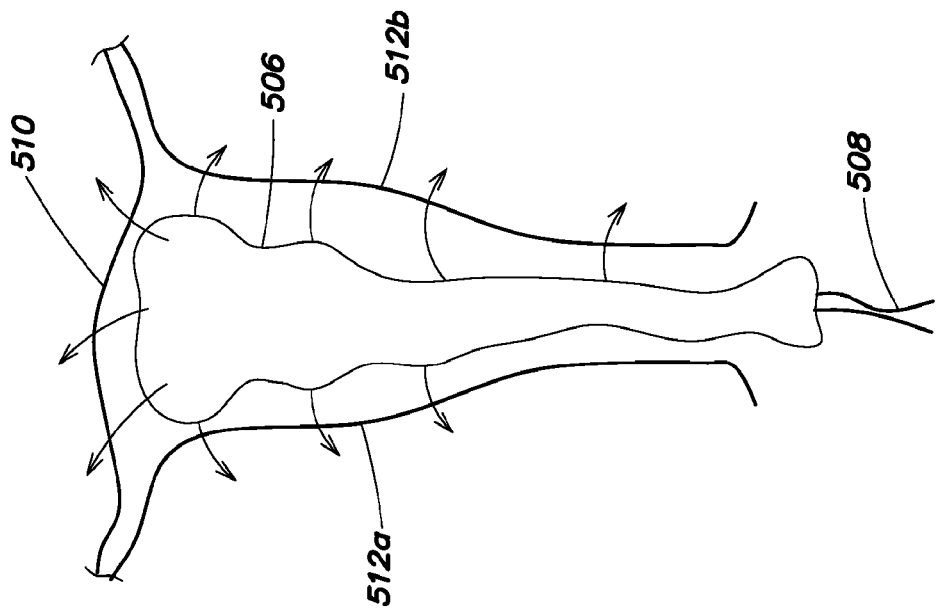
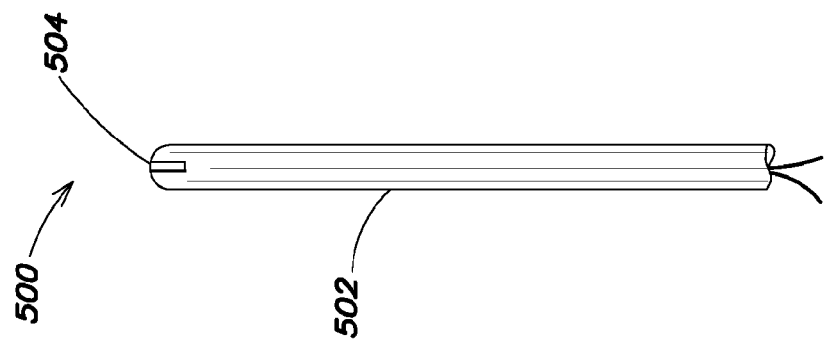
FIG. 5B
FIG. 5A

ABLATION DEVICE USING BIPOLAR STEAM GENERATION

RELATED APPLICATIONS DATA

The present application is a National Phase entry under 35 U.S.C § 371 of International Patent Application No. PCT/US2013/060613, having an international filing date of Sep. 19, 2013, which claims the benefit of priority under 35 U.S.C. § 119 to U.S. Provisional Patent Application No. 61/702,926, filed Sep. 19, 2012, and which is hereby incorporated by reference in its entirety.

BACKGROUND

Ablation devices are used to ablate tissue inside a patient's body. For example, endometrial ablation devices ablate the endometrial lining of the uterus and some portion of the myometrium of the uterus through application of electrical current applied directly to the tissue. The application of electrical current directly to the tissue increases the temperature of the tissue and causes water in the tissue to boil, thereby generating steam. Areas of the uterine cavity that are not in direct contact with the electrodes that supply the current may also be ablated by contact with the steam generated by the electrical current applied to the tissue. However, there are disadvantages to such devices, such as, for example, the ablation of the tissue may not be uniform due to variations in electrical current density on the surface and near the border of the electrodes. In addition, high current densities at the electrode surface can lead to more ablation of the lining than desired.

SUMMARY

Aspects and embodiments for ablating tissue through the generation of steam are disclosed herein. Various intrauterine ablation devices and methods to ablate the lining of a uterus through the generation of steam in the uterine cavity are disclosed.

According to one embodiment, an ablation device includes an absorbent medium positioned between two electrodes. According to one aspect, a conductive fluid can be dispensed into an absorbent medium in the device after insertion of the device into the patient through a fluid tube. According to another aspect, the conductive fluid can be provided to the absorbent medium in the device before the device is inserted into the patient.

According to one aspect, an ablation device comprises a first permeable electrode having a first electrode connector, a second permeable electrode having a second electrode connector; an absorbent medium positioned between the first and second permeable electrodes, and configured to absorb a conductive fluid, and a permeable spacer adjacent to each of the first and second permeable electrodes. In one embodiment, the permeable spacer is configured to enclose the first and second permeable electrodes.

According to at least one embodiment, the ablation further comprises a sheath that is configured to enclose the first and second permeable electrodes, the absorbent medium, and the permeable spacer in a collapsed position.

According to at least one embodiment, the ablation further comprises a fluid conduit configured to provide the conductive fluid to the absorbent medium. According to at least one embodiment, the ablation further comprises at least one suction tube configured to channel any of fluid, steam, and vapor away from the first and second permeable electrodes. Aspects of such embodiment include that the ablation device is sized and arranged to be an intrauterine ablation device and so that the at least one suction tube can be positioned and arranged to be near a fallopian tube opening when in use. Further aspects of such embodiment include a suction device configured to be coupled to the at least one suction tube to remove the any of the fluid, steam, and vapor away from the first and second permeable electrodes through the suction tube to create a low pressure region at the fallopian tube opening. Additional aspects include that the suction device further comprises a controller that is configured to create any of continuous, intermittent, and cyclical suction. In further embodiments, the suction need not be active. For example, the cavity can be evacuated passively.

According to at least one embodiment, the first and second permeable electrodes are planar electrodes disposed on opposite sides of the absorbent medium.

According to at least one embodiment, the permeable spacer includes the absorbent medium.

According to at least one embodiment, the ablation further comprises a radiofrequency power source coupled to the first and second electrode connectors and configured to supply a current to the first and second permeable electrodes, the radiofrequency power source further comprising a controller that is configured to control the supply of current to the first and second permeable electrodes. Aspects of such embodiment include that the controller is configured to supply the current any of continuously, intermittently, and cyclically.

According to at least one embodiment, the device is sized and arranged to be an intrauterine ablation device. In addition, according to at least one embodiment, the absorbent medium can include an osmotic dilator. Further, according to one at least one embodiment, the intrauterine ablation device can comprise an eluting component configured to administer an anesthetic to a patient.

According to another aspect, an ablation device is sized and arranged to be an intrauterine ablation device, the ablation device comprises an absorbent medium configured to absorb a conductive fluid, a first electrode having a first electrode connector; and a second electrode having a second electrode connector.

According to at least one embodiment, the intrauterine ablation device further comprises a sheath that is configured to enclose the first and second electrodes and the absorbent medium in a collapsed state.

According to at least one embodiment, the intrauterine ablation device further comprises a fluid conduit configured to provide the conductive fluid to the absorbent medium.

According to at least one embodiment, the intrauterine ablation device further comprises at least one suction tube configured to channel any of fluid, steam, and vapor away from the first and second electrodes and the absorbent medium. Aspects of such embodiment include that the at least one suction tube can be positioned and arranged to be near a fallopian tube opening when in use. Additional aspects of such embodiment include that the at least one suction tube comprises two suction tubes, each positioned and arranged to be near a fallopian tube opening when in use. Further aspects of such embodiment can include a suction device that is configured to couple to the at least one suction tube to remove the any of fluid, steam, and vapor away from the first and second electrodes and the absorbent medium through the suction tube to create a low pressure region at the fallopian tube opening. Further aspects of such embodiment can include that the suction device comprises a controller that is configured to create any of continuous, intermittent, and cyclical suction.

According to at least one embodiment of the intrauterine ablation device the first and second electrodes are permeable planar electrodes disposed on opposite sides of the absorbent medium.

According to at least one embodiment, the intrauterine ablation device further comprises a permeable spacer adjacent to each of the first and second permeable electrodes, wherein the permeable spacer is configured enclose the first and second permeable electrodes and the absorbent medium.

According to at least one embodiment of the intrauterine ablation device, the first and second electrodes are flexible electrodes and the absorbent medium is an expandable medium that is configured to distend with absorption of the conductive fluid.

According to at least one embodiment of the intrauterine ablation device, the first and second electrodes are flexible circular conductors disposed in parallel within the absorbent medium to comprise a coiled probe assembly.

According to at least one embodiment, the intrauterine ablation device further comprises a radiofrequency power source coupled to the first and second electrode connectors and configured to supply a current to the first and second electrodes, the radiofrequency power source further comprising a controller that is configured to control the supply of current to the first and second permeable electrodes. Aspects of such embodiment include that the controller is configured to supply the current any of continuously, intermittently, and cyclically.

According to one aspect a method of endometrial ablation is provided. The method comprises inserting an ablation device into a uterine cavity, the ablation device comprising an absorbent medium configured to absorb a conductive fluid, a first electrode having a first electrode connector and a second electrode having a second electrode connector; introducing conductive fluid into the uterine cavity and into absorbent medium; and applying energy between the first and second electrode connectors to at least partially vaporize the conductive fluid so as to ablate at least a portion of an endometrial lining of the uterine cavity.

According to at least one embodiment, introducing the conductive fluid into the uterine cavity comprises providing a predefined amount of the conductive fluid into the absorbent medium. According to at least one embodiment, the method further comprises waiting a period of time after providing the conductive fluid to the absorbent medium to allow for substantially uniform absorption of the conductive fluid by the absorbent medium. According to at least one embodiment, the method further comprises suctioning fluid from the absorbent medium before applying energy.

According to at least one embodiment, the act of vaporizing of the conductive fluid occurs within the uterine cavity. According to one embodiment, the act of vaporizing the conductive fluid comprises passing the vaporized fluid through the first and second electrodes, which are permeable electrodes. According to at least one embodiment, the method further comprises preventing the first and second electrodes from contacting tissue of the uterine cavity with a spacer. According to at least one embodiment, the method further comprises distending the absorbent medium by absorbing the conductive fluid with the absorbent medium so as to at least partially fill the uterine cavity with the absorbent medium and the first and second electrodes.

According to at least one embodiment, the method further comprises administering an anesthetic to the patient through an eluting component of the intrauterine ablation device.

According to at least one embodiment, the method further comprises providing the absorbent medium as an osmotic dilator.

According to at least one embodiment, the method further comprises distending the absorbent medium through osmosis.

Still other aspects, embodiments, and advantages of these exemplary aspects and embodiments, are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE FIGURES

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures:

FIG. 2A is a top view of an embodiment of an intrauterine therapy application device in a retracted position inside a uterus, according to aspects of the invention;

FIG. 2B is a top view of the embodiment of the intrauterine therapy application device of FIG. 2A in a partially expanded position inside a uterus, according to aspects of the invention;

FIG. 2C is a top view of the embodiment of the intrauterine therapy application device of FIG. 2A in a substantially fully expanded position inside a uterus, according to aspects of the invention;

FIG. 2D is an exploded view of an absorbent material and electrodes of the intrauterine therapy application device of FIG. 2A, according to aspects of the invention;

FIG. 4A is a top view of another embodiment of an intrauterine therapy application device, according to aspects of the invention;

FIG. 4B is a top view of the intrauterine therapy application device of FIG. 4A positioned in a uterus, according to aspects of the invention;

FIG. 5A is a top view of a short-term implant for providing a medicament in a retracted position, according to aspects of the invention;

FIG. 5B is a top view of the short-term implant of FIG. 5A in an expanded position inside a uterus, according to aspects of the invention.

DETAILED DESCRIPTION

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure.

According to aspects of this disclosure, various structures and methods are provided herein for ablating tissue inside the uterus of a patient with the generation of steam or a vapor. In particular, various embodiments, structures and methods are provided to ablate the lining of the uterus through the generation of steam or a vapor in the uterine cavity without the need to apply current directly to uterine cavity tissue. In at least one embodiment, an ablation device includes an absorbent medium for absorbing a conductive fluid and at least two electrodes for applying a current between the at least two electrodes so as to convert the conductive fluid absorbed in the absorbent medium to a steam or vapor. The vapor or steam is generated in the uterus after the ablation device is inserted in the uterus. For example, after the ablation device is inserted in the uterus the absorbent medium can be provided with a conductive fluid and current is applied to the electrodes and the absorbent medium thereby causing the conductive fluid in the absorbent medium to vaporize. With such an arrangement, the steam or vapor is generated so as to ablate the endometrial lining and at least some portion of the myometrium of the uterus. Various embodiments, structures and methods for providing the conductive fluid to the absorbent medium are provided. In addition, various embodiments, structures and methods for providing suction to the uterine cavity, to the absorbent medium, and to an area of the electrodes are provided.

One advantage of such aspects and embodiments is that ablation is accomplished by generation of a steam or vapor and electrodes need not be in direct contact with uterine tissue. Another advantage of such aspects and embodiments is that RF electrical current need not be transmitted directly to the uterine tissue. Still another advantage of such aspects and embodiments is that endometrial ablation may be provided in large or irregularly shaped uterine cavities or cavities where fibroids are present. Still another advantage of such aspects and embodiments is that that the buildup of steam can be controlled so that it is not excessive and so that the condensation of steam (or collection of condensate) in the cavity is not such that it would interfere with the uniformity of the ablation.

Figure 1A:
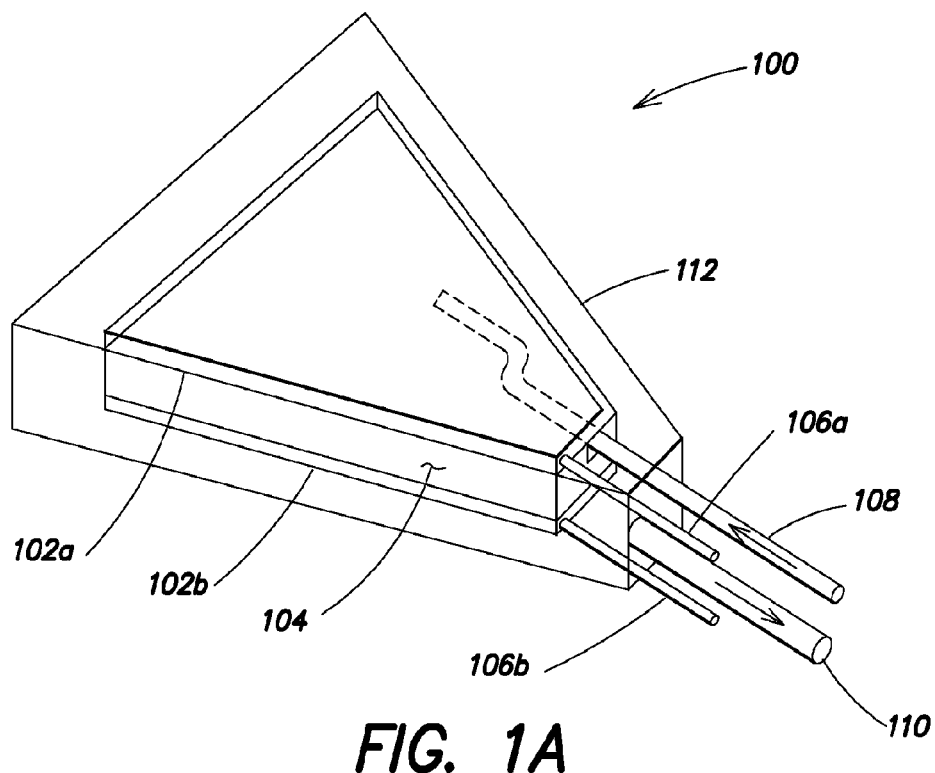
FIG. 1A is a side elevation view of an embodiment of an intrauterine therapy application device in an expanded position, according to aspects of the invention.

Referring now to the Figures, FIG. 1A is a side elevation view of an intrauterine ablation device 100 in an expanded position according to one embodiment of the disclosure. The intrauterine ablation device 100 includes first 102a and second 102b electrodes, an absorbent medium 104, first 106a and second 106b electrode connectors, an input tube 108 for providing a fluid to the ablation device and a suction tube 110 for withdrawing fluids and gases from the ablation device and/or a uterine cavity of a patient. According to aspects of this embodiment, the electrodes 102a, 102b can be permeable electrodes that allow fluid, vapor or steam to permeate the electrodes and flow through them. According to aspects of this embodiment, the device 100 also includes a permeable spacer 112 that allows fluid, vapor or steam to permeate and flow through it. The permeable spacer also spaces the intrauterine ablation device 100 away from the tissue of the uterine cavity. In the illustrated embodiment, the absorbent medium 104 is positioned between the first 102a and second 102b electrodes, but it is to be appreciated that other arrangements of the electrodes and the absorbent medium can be provided, some of which are disclosed herein.

As shown in FIG. 1A, the intrauterine ablation device 100 is illustrated in an expanded position, for example, as it would be in use inside a patient's uterine cavity. It should also be appreciated that according to some aspects of the disclosure, certain embodiments of the intrauterine ablation device can also have a retracted position wherein the intrauterine ablation device is collapsed inside an outer sheath or probe, which allows for insertion of the intrauterine ablation device in the uterine canal of a patient and also provides for extending of the intrauterine ablation device beyond the sheath or probe so that it can expand into the expanded position for use inside the uterine cavity.

For the illustrated embodiment, the absorbent medium 104 can be provided with a conductive fluid, such as water or saline, which can be converted to steam or vapor by establishing a current between the electrodes 102a, 102b. As will be discussed herein, the absorbent medium can be provided with the conductive fluid either before and/or during an ablation procedure. A current can be provided to the electrodes 102a, 102b by coupling a current source to the electrodes at electrode connectors 106a, 106b, thereby establishing a current between the electrodes 102a, 102b. For example, according to at least one embodiment a radiofrequency (RF) voltage and current can be applied to the electrodes 102a, 102b by coupling the electrodes at connectors 106a, 106b to an RF signal source. It is to be appreciated that the current and voltage levels applied to the electrodes 102a, 102b can be controlled to limit an amount of energy delivered to the patient. According to aspects of the disclosure, the current and voltage control may be manually controlled or automatically controlled by a controller. According to at least one embodiment, the RF current and voltage levels may also be measured and provided to a controller as part of a control loop to limit the total energy delivered to the tissue of a patient. One embodiment of a controller arrangement of the voltage and current source can be configured to supply the current to the electrodes any of continuously, intermittently, and/or cyclically. The ablation device may also include structure known to those of skill in the art to selectively or globally measure the impedance of the tissue that is to be ablated any of before, during and after ablation, any of continuously or intermittently, and any of in association with modulation of the suction level or not, so as to provide a feedback loop to the controller in order to control an amount and/or depth of tissue to be ablated.

According to at least one embodiment, suction may be applied to the uterine cavity of a patient through the suction tube 110 coupled to a vacuum source (not illustrated) to remove fluids or vapor from the uterus. For example, suction can also be used to remove any of the conductive fluid that has previously been dispensed to the uterus through the absorbent medium, bodily fluids, blood, moisture, vapor, steam, ablated uterine tissue, or other matter. According to aspects of the illustrated embodiment, a distal end of the suction tube 110 may be positioned, for example, at any of a base of the electrodes 102a, 102b, or located in the permeable space 112, or manually positioned by the user. As will be discussed further herein, according to some embodiments of the ablation device, the suction tube 110 can be one or more suction tubes, and the at least one suction tube can be configured and arranged with respect to the intrauterine ablation device so that a distal end of the suction can be positioned near an opening of a fallopian tube of a patient, when the intrauterine ablation device is inserted into the cervical canal of a patient and is in its expanded position. One advantage of such embodiments that include at least one suction tube is that that a buildup of steam or vapor can be controlled so that is not excessive and so that the condensation of steam (or collection of condensate) in the cavity would not interfere with the uniformity of the ablation.

As illustrated in FIG. 1A, the intrauterine ablation device is provided with the permeable spacer 112 that surrounds the electrodes 102a, 102b and the absorbent medium 104. According to aspects of this embodiment, the permeable spacer 112 prevents the electrodes 102a, 102b from directly contacting uterine tissue of the patient, which can aide in preventing direct transmission of electrical current to the tissue. In at least one embodiment, the permeable spacer is composed of a same permeable material as the absorbent medium 104. Further, in at least one embodiment the permeable spacer 112 is continuous with and comprises the absorbent medium 104.

According to one aspect of various embodiments of the intrauterine ablation device of this disclosure, it is appreciated that using steam to ablate uterine tissue can be more effective in ablating the uterine tissue than direct application of a current to the tissue, especially in large or irregularly shaped uterine cavities, or cavities where fibroids are present. Further, there is no need for direct contact of the electrodes, such as electrodes 102a, 102b, with the uterine tissue.

Figure 1B:
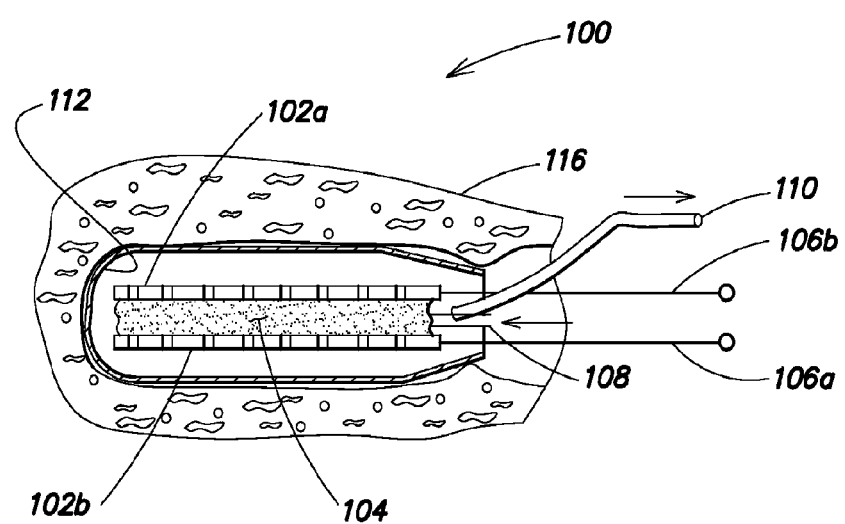
FIG. 1B is a schematic representation of a side view of the intrauterine therapy application device of FIG. 1A, according to aspects of the invention.

FIG. 1B is a schematic representation of a side view of the intrauterine therapy application device of FIG. 1A, illustrated as inserted into a uterus. As shown in FIG. 1B, the permeable spacer 112 may contact the uterine tissue 116. According to one aspect of the illustrated embodiment, it is appreciated that both uterine tissue 116 in contact with the permeable spacer 112 and uterine tissue that is not in contact with the permeable spacer 112 can be ablated by steam generated by the illustrated ablation device 100. This is because the ablation is accomplished by generation of a steam or vapor with the ablation device itself, not by providing current directly to the uterine tissue so as to generate a steam or vapor, and thus the electrodes need not be in direct contact with uterine tissue to ablate the uterine tissue. One advantage of such aspects and embodiments is that RF current need not be transmitted directly to the uterine tissue. Another advantage of such aspects and embodiments is that endometrial ablation may be provided in large or irregularly shaped uterine cavities including, for example, arcuate, septate, assymetrical, anteflexed, or retroflexed uterior in cavities where fibroids and or polyps are present.

According to aspects of the illustrated embodiment of the intrauterine therapy application device, a conductive fluid can be provided to the absorbent medium 104 before and/or during an ablation procedure. For example, the conductive fluid can be applied to and allowed to impregnate the absorbent medium 104 of the device before insertion of the device 100 in the uterine cavity of a patient. Further, the conductive fluid can be dispensed into the absorbent medium 104 through the input tube 108 after the device 100 has been inserted into a patient. According to various embodiments, the tube 108 can be a single tube or multiple tubes that are for example embedded in the absorbent medium 104. In one example, the conductive fluid can be continuously dispensed into the absorbent medium 104 during an ablation procedure, and the RF voltage and current can be continuously applied to the device so that the generation of steam is continuous. In another example, the conductive fluid can be intermittently dispensed into the absorbent medium 104 during an ablation procedure, and the RF voltage and current can be intermittently applied so that the generation of steam is intermittent. In another example, the conductive fluid can dispensed into the absorbent medium 104 after the device 100 is inserted into a patient, but before ablation begins, to impregnate the absorbent medium 104 of the device before ablation. For such use, a user of the device may wait a sufficient period of time to allow the fluid to evenly diffuse into the absorbent medium. One advantage of dispensing the conductive fluid into the absorbent medium 104 before ablation begins and allowing the fluid to evenly diffuse is that it can result in more uniform steam generation over the surface area of the uterine cavity during ablation.

It is also appreciated that it is not necessary to provide a conductive fluid to the absorbent medium during ablation for any of the embodiments disclosed herein. According to aspects of any of the embodiments disclosed herein, it may be preferable to pre-dispense the conductive fluid to the absorbent medium and allow the conductive fluid to substantially evenly diffuse in the absorbent medium before ablation, as introducing the fluid during the ablation may cause temperature variations across the absorbent medium and electrodes, and thus may cause potential non-uniform ablation.

According to aspects of the embodiment of FIGS. 1A-1B, fluid may be dispensed through the at least one tube 108 to the absorbent medium 104 prior to ablation, and the volume of the fluid dispensed may be pre-determined to correspond with the volume of the absorbent medium 104. After the fluid is dispensed into the absorbent medium, a user may wait a predetermined period of time before beginning ablation. During the predetermined period of time, the fluid may more evenly disperse throughout the absorbent medium 104. According to at least one aspect, the suction tube 110 may be used to create a vacuum or a partial vacuum in the uterine cavity in order to remove any excess fluid from the absorbent medium, to provide a more precise amount of fluid in the absorbent medium 104, and which may also help to distribute fluid more evenly in the absorbent medium.

According to another aspect of the intrauterine therapy application device disclosed herein, bodily fluid from the surrounding tissue and cavity of a patient may be absorbed by the absorbent medium 104. With such an arrangement, after the device is inserted into a patient, the user may wait a predetermined period of time before beginning ablation in order to allow for sufficient fluid absorption by the absorbent medium 104. As discussed above, the suction tube 110 may be used to create a vacuum or a partial vacuum in the uterine cavity in order to remove any excess fluid, to provide a more precise amount of fluid in the absorbent medium 104, and to allow the fluid to be distributed more evenly throughout the absorbent medium 104.

According to another aspect of at least one embodiment of the intrauterine therapy application devices disclosed herein, fluid dispensed into the absorbent medium may distend the absorbent medium thereby providing for the intrauterine therapy application device to more uniformly fill the uterine cavity to provide for uniform ablation. FIG. 2A is a top view of an intrauterine therapy application device 200 having a distending absorbent medium 202 illustrated in an non-distended position and illustrated as having been inserted inside a uterus of a patient. According to one feature of this embodiment, the device 200 has a smaller diameter in the non-distended position than in a distended position, which allows for it to be inserted transcervically into the uterine cavity of the patient. The device 200 need not have a sheath or probe for insertion into the uterine canal. However, it is appreciated that according to at least one embodiment, the intrauterine ablation device can also have a retracted position wherein the intrauterine ablation device is collapsed inside a sheath or probe, which allows for insertion of the sheath or probe in the uterine canal of a patient and also provides for extending of the intrauterine ablation device beyond the sheath or probe so that it can expand into the uterine cavity in the non-distended position as shown in FIG. 2A.

According to additional aspects of this embodiment of the intrauterine ablation device, the absorbent medium 202 is configured of a material that absorbs fluid and distends into a distended position. FIG. 2B is a top view of the intrauterine device 200 of FIG. 2A in a partially distended position inside a uterus after partial absorption of a fluid in the absorbent medium. FIG. 2C is a top view of the intrauterine device 200 in a fully distended position inside a uterus. In the fully distended position, the intrauterine device 200 may fill the uterine cavity. As shown in the exploded view of FIG. 2D, for at least one embodiment the absorbent medium 202 can be positioned between two expandable electrodes 204a, 204b. However, it is to be appreciated that alternate arrangements such as electrodes that not expandable or that maintain a certain spacing between them are also contemplated by this disclosure.

According to one aspect of the illustrated device, after the device is inserted into a patient in the non-distended position, the user may wait a predetermined period of time before beginning ablation in order to allow for sufficient fluid absorption by the absorbent medium 202 to at least a partially distended position as shown in FIG. 2B or a fully distend position as shown in FIG. 2C. It is to be appreciated that the distention effect of the absorbent medium 202 may be caused by osmotic dilation, where bodily fluid from the surrounding tissues of a patient can be absorbed by the absorbent medium to at least a partially distend the absorbent medium. Alternatively, and/or in addition to the osmotic dilation, a conductive fluid can be dispensed into the absorbent medium 202 after the device 200 has been inserted into a patient. It is to be appreciated that the conductive fluid can be provided to the absorbent medium before ablation begins and allowed to more evenly diffuse in the absorbent medium, and/or during an ablation procedure. For example, a conductive fluid can applied to the absorbent medium 202 via the input tube 208 after the device 200 has been inserted into a patient, so as to impregnate the absorbent medium 202 and so as to distend the absorbent medium to at least a partially distended position. According to aspects of this embodiment, the conductive fluid can also be any of continuously dispensed into the absorbent medium 202 during an ablation procedure or intermittently dispensed into the absorbent medium 202 during an ablation procedure so as to provide either continuous or intermittent steam or vapor generation.

It is also to be appreciated that it is not necessary to provide conductive fluid to the absorbent medium during ablation for any of the embodiments disclosed herein. According to aspects of the illustrated embodiment, it may be preferable to pre-dispense the conductive fluid to the absorbent medium before ablation as introducing the fluid during the ablation may cause temperature variations across the absorbent medium and potential non-uniform ablation. For the embodiment of FIGS. 2A-2C, a conductive fluid may be dispensed through the at least one tube 208 to the absorbent medium 202 prior to ablation, and the volume of the fluid dispensed may be pre-determined to correspond with the volume of the absorbent medium 202. After the fluid is dispensed into the absorbent medium, a user may wait a predetermined period of time before beginning ablation. During the predetermined period of time, the fluid may more evenly disperse throughout the absorbent medium 202.

According to aspects of this embodiment, at least one suction tube 210 can be provided and coupled to a vacuum source, which may be used to create a vacuum or a partial vacuum in the uterine cavity in order to remove any excess fluids or vapor from the uterus and to allow the conductive fluid to be distributed more evenly throughout the absorbent medium 202. In addition, the at least one suction tube can also be used to remove any of the conductive fluid that has previously been dispensed to the uterus through the absorbent medium, bodily fluids, blood, moisture, vapor, steam, ablated uterine tissue, or other matter. According to at least one embodiment, as discussed further infra, the at least one suction tube may comprise two suction tubes, each positioned and arranged to be near a fallopian tube opening when in use, which can prevent unwanted ablation or fluid or steam build up near the fallopian tube openings. Further, the suction device may comprise a controller that is configured to create any of continuous, intermittent, and cyclical suction. According to at least one aspect, the at least one suction tube and vacuum controller may be used to remove any excess fluid from the absorbent medium, to provide a more precise amount of fluid in the absorbent medium, and which may also help to distribute fluid more evenly in the absorbent medium.

According to various aspects of the illustrated embodiment, a current can be provided to the electrodes 204a, 204b thereby establishing a current between the electrodes so as to covert the conductive fluid to a steam and or vapor for ablation. For example, according to at least one embodiment a radiofrequency (RF) voltage and current signal can be applied to the electrodes 204a, 204b. It is to be appreciated that the current and voltage levels applied to the electrodes 204a, 204b can be controlled to limit an amount of energy delivered to the patient. According to aspects of the disclosure, the current and voltage control may be manually controlled or automatically controlled by a controller. According to at least one embodiment, the RF current and voltage levels may also be measured and provided to a controller as part of a control loop to limit the total energy delivered to the tissue of a patient. With a controlled voltage and current source, the controller can be configured to supply the current to the electrodes any of continuously, intermittently, and cyclically.

Figure 3A:
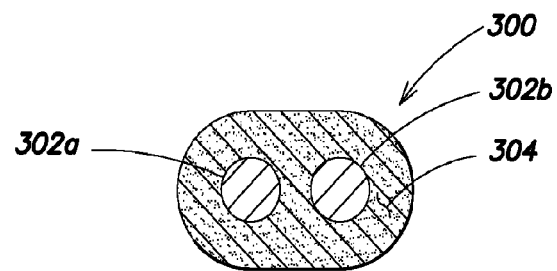
FIG. 3A is a cross-sectional view of an embodiment of an elongated intrauterine therapy application probe, according to aspects of the invention.

According to another embodiment of an intrauterine ablation device, the absorbent medium and electrodes may be make up an elongated flexible probe that bends and curls when inserted in the uterine cavity. FIG. 3A is a cross-sectional view of an elongated intrauterine ablation probe 300 according to one such embodiment. The elongated intrauterine probe 300 includes conductors 302a, 302b and an absorbent medium 304. According to one aspect of the illustrated embodiment, the conductors 302a, 302b may be flexible conductors and the absorbent medium may also function as a spacer between the flexible conductors and/or an insulator of the flexible conductors to prevent direct transmission of current from the flexible conductors 302a, 302b to patient's tissue.

Figure 3B:
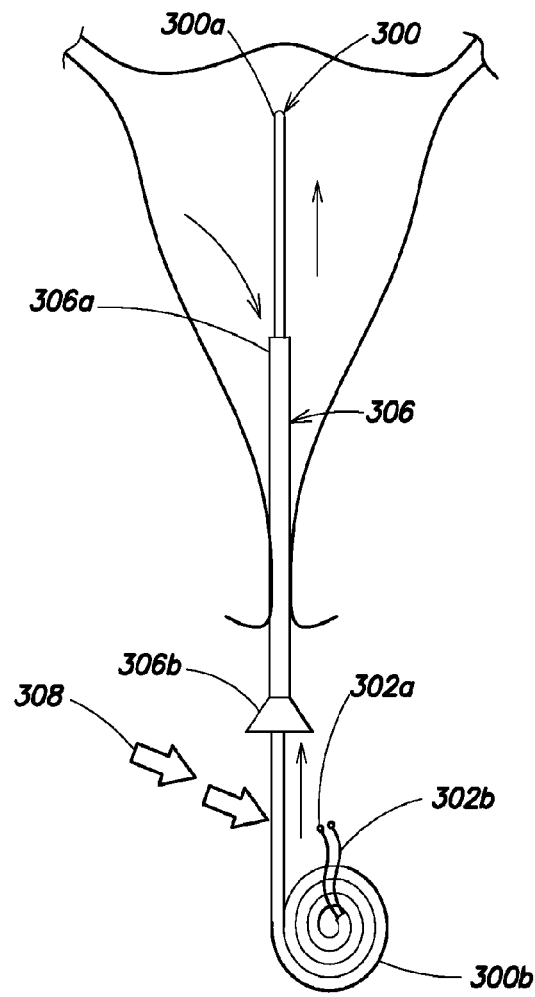
FIG. 3B is a top view of the elongated intrauterine therapy application probe of FIG. 3A with a distal end of the ablation probe extended from the sheath and into a uterus, according to aspects of the invention.

FIG. 3B is a top view of the elongated ablation probe 300 of FIG. 3A housed within a sheath 306. As illustrated, the sheath has a distal end 306a which is illustrated as inserted in a uterine cavity of a patient with a distal end 300a of the probe 300 extending beyond the distal end of the sheath 306 into the uterine cavity. According to one aspect of at least one embodiment, fluid can be dispensed to the absorbent medium 304 of the elongate probe 300 as it enters the sheath 306 at a proximate end 306b, so as to permeate the absorbent medium and create distention of the absorbent medium once inserted into the uterine cavity. According to one aspect of the illustrated embodiment, a proximal end 300b of the probe 300 is coiled up before it is fed into the uterine cavity through the sheath 306. According to one aspect of the illustrated embodiment, the sheath 306 may also include a suction tube, as described above with respect to FIGS. 1A-1B and 2A-2C.

Figure 3D:
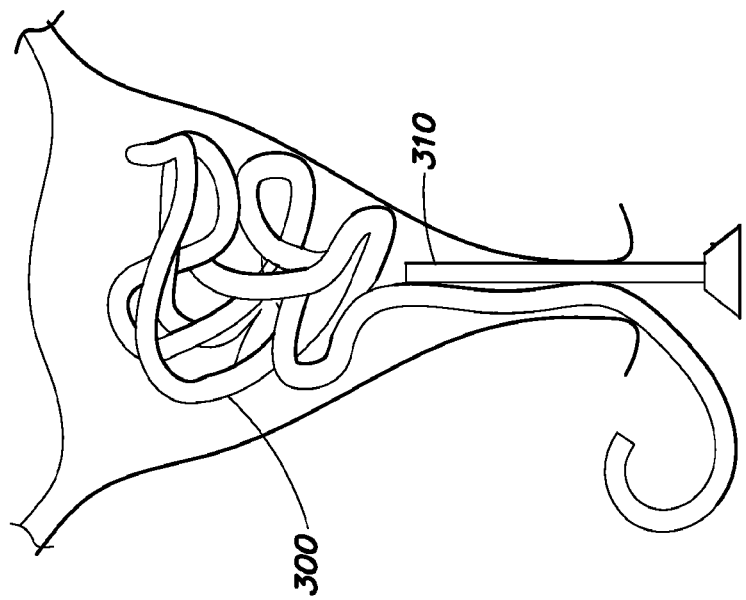
FIG. 3D is a top view of the elongated intrauterine therapy application probe of FIG. 3A and a hysteroscope in place to view the deployment and positioning of the probe, with the ablation probe partially uncoiled inside a uterus, according to aspects of the invention.
Figure 3C:
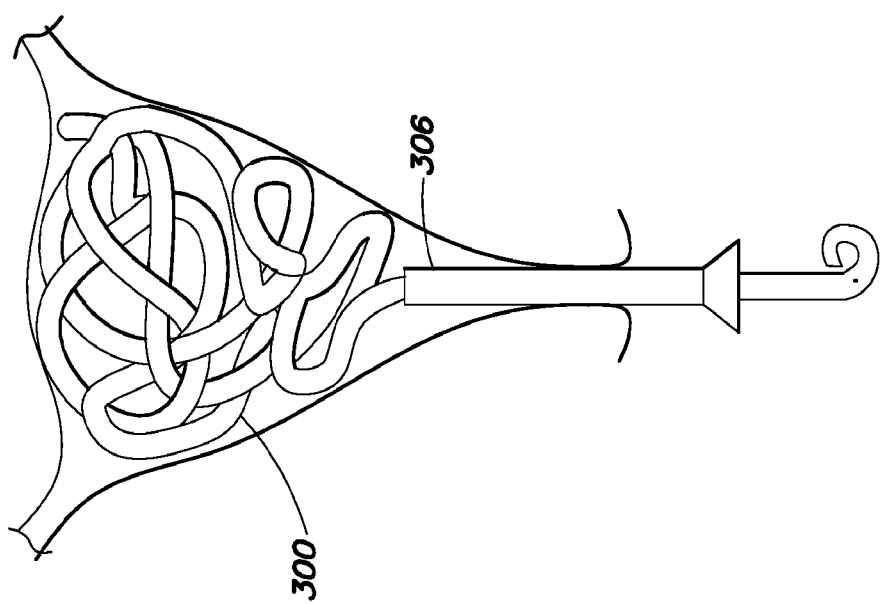
FIG. 3C is a top view of the elongated intrauterine therapy application probe of FIG. 3A with the ablation probe substantially fully uncoiled inside a uterus, according to aspects of the invention.

FIG. 3C is a top view of the elongated probe 300 fully uncoiled inside a uterus of a patient. The elongated probe 300 is uncoiled as it is fed through the sheath 306. Once inside the uterus, the probe 300 bends and wraps to fill the uterine cavity. As noted herein with respect for other embodiments of an intrauterine ablation device, the conductors 302a and 302b can be provided with a current so as to heat up the fluid absorbed in the absorbent medium 304 of the elongated probe, so as to convert the fluid to steam or vapor and so as to ablate the uterine tissue.

FIG. 3D is a top view of the probe 300 uncoiled inside a uterus to partially fill the uterine cavity. According to one aspect of this embodiment of the elongated ablation probe, the probe 300 need not fill the entire uterine cavity so long as there is sufficient fluid in the absorbent medium 304 of the probe 300 so as to create a sufficient amount of steam for ablation. As shown in FIG. 3D, according to aspects of any of the various embodiments disclosed herein, after the probe 300 has been inserted in the uterus of the patient, the sheath 306 may be removed and a scope 310 may be inserted into the uterus to monitor the uterus during the ablation procedure. For example, the scope 310 may allow a user to visualize the placement of the probe 300 in the uterus. The scope 310 may also be used to determine both proper placement of the probe 300 and sufficient filling of the uterine cavity with the elongated probe 300 for ablation.

According to at least one embodiment of the elongated probe 300 of FIGS. 3A-3B, bodily fluids from the surrounding tissues of a patient can be absorbed by the absorbent medium 304 once the probe has been extended inside the uterine cavity of the patient, and/or fluid can be dispensed to the absorbent medium 304 of the elongate probe. For example, conductive fluid can be provided to the absorbent medium 304 as it enters the sheath 306 at proximate end 306b. The conductive fluid can be provided to the absorbent medium before ablation begins, and the volume of the fluid dispensed may be pre-determined to correspond with the volume of the absorbent medium 304. After the fluid is dispensed into the absorbent medium, a user may wait a predetermined period of time before beginning ablation so that the fluid may more evenly disperse throughout the absorbent medium 304. It is also to be appreciated that it is not necessary to provide conductive fluid to the absorbent medium 304 during ablation. According to aspects of this embodiment, it may be preferable to pre-dispense the conductive fluid to the absorbent medium before ablation.

According to aspects of this embodiment, at least one suction tube can be provided and coupled to a vacuum source to create a vacuum or a partial vacuum in the uterine cavity in order to remove any excess fluids or vapor from the uterus and to allow the fluid to be distributed more evenly throughout the absorbent medium 304. For example, at least one suction tube can also be used to remove any of the conductive fluid that has previously been dispensed to the uterus through the absorbent medium, bodily fluids, blood, moisture, vapor, steam, ablated uterine tissue, or other matter. According to at least one embodiment, the at least one suction tube may comprise two suction tubes, each positioned and arranged to be near a fallopian tube opening when in use. Further, the suction device may comprise a controller that is configured to create any of continuous, intermittent, and cyclical suction.

According to various aspects of this embodiment, a current can be provided to the electrodes 302a, 302b thereby establishing a current between the electrodes so as to covert the conductive fluid to a steam and or vapor for ablation. For example, according to at least one embodiment a radiofrequency (RF) voltage and current can be applied to the electrodes 302a, 302b. It is to be appreciated that the current and voltage levels applied to the electrodes 302a, 302b can be controlled to limit an amount of energy delivered to the patient. According to aspects of the disclosure, the current and voltage control may be manually controlled or automatically controlled by a controller. According to at least one embodiment, the RF current and voltage levels may also be measured and provided to a controller as part of a control loop to limit the total energy delivered to the tissue of a patient. With a controlled voltage and current source, the controller can be configured to supply the current to the electrodes any of continuously, intermittently, and cyclically.

As noted above, an intrauterine ablation device need not occupy an entire volume of a uterine cavity to provide ablation. In such embodiments where the ablation device does not occupy the entire cavity, positioning of the ablation device can be desirable. FIG. 4A is a partial top view of an intrauterine ablation device 400 including an intrauterine ablation device 402 having deployment arms 406a, 406b. The intrauterine ablation device 402 can include any of the embodiments of an absorbent medium (not illustrated), first 412a and second 412b electrodes, a permeable spacer (not illustrated), an input tube (not illustrated), and at least one suction tube 414, as has been discussed herein with respect to the embodiments illustrated in FIGS. 1A-1B, 2A-2B.

The deployment arms 406a, 406b as illustrated in FIG. 4A may be used with any of the herein described embodiments to axially fix the intrauterine ablation device's position in the uterus. In one embodiment, the intrauterine ablation device 400 is inserted into a sheath 410 with the deployment arms 406a, 406b in a retracted position inside the sheath 410. The sheath 410 can be inserted into the uterine canal of a patient and into the uterine cavity of the patient, as illustrated in FIG. 4B, and the intrauterine ablation device 400 and the deployment arms 406a, 406b can be extended beyond a distal end of the sheath into the uterine cavity so that the deployment arms 406a, 406b expand within the uterus. The intrauterine ablation device 400 can also include a cervical collar 408 at the proximal end of the sheath 410 that helps position the sheath and the intrauterine ablation device within the uterus. In particular, the cervical collar 408 can prevents the device 400 from being inserted too far into the uterus. According to aspects of one embodiment, the cervical collar 408 has a wider diameter than the sheath 410, and the wider diameter cervical collar 408 does not pass through or into the cervical canal.

FIG. 4B is a top view of the intrauterine device 400 inserted into a uterus. As shown in FIG. 4B, the deployment arms 406a, 406b do not touch the fundus of the uterus, and there is a space 418 between the fundus of the uterine cavity and a distal end the intrauterine ablation device 400. As illustrated in FIG. 4B, the intrauterine ablation device 400 includes a first suction tube 414a and a second suction tube 414b, each being positioned with a distal end of the tube proximate a respective fallopian tube opening to create a low pressure region 416a, 416b at the respective fallopian tube opening. According to one feature of this embodiment of the intrauterine ablation device, the low pressure regions 416a, 416b resulting from the positioning of the respective first suction tube 414a and second suction tube 414b act to prevent steam from escaping up the fallopian tubes, thereby protecting the patient from undesired fallopian tube damage and improving the safety of the ablation procedure. For sizing and positioning of the device via the deployment arms 406a, 406b and/or the cervical plug 408, a sounding length 420 (the distance from the proximal end of the cervix to the fundus of the uterus) is measured and the deployment arms 406a, 406b and/or the cervical plug 408 of the device are adjusted, before the device 400 is inserted in the patient.

As has been noted herein with respect to the various disclosed embodiments, for the intrauterine therapy application device 400 a conductive fluid can be provided to its absorbent medium before and/or during an ablation procedure. For example, the conductive fluid can be applied to and allowed to impregnate the absorbent medium of the device before insertion of the device in the uterine cavity of a patient, and/or the conductive fluid can be dispensed into the absorbent medium through an input tube after the device has been inserted into a patient. The conductive fluid can be continuously dispensed into the absorbent medium during an ablation procedure, can be intermittently dispensed into the absorbent medium during an ablation procedure, or can dispensed into the absorbent medium after the device 400 is inserted into a patient, but before ablation begins.

For the embodiment of FIGS. 4A-4B, fluid may be dispensed through the at least one tube to the absorbent medium prior to ablation, and the volume of the fluid dispensed may be pre-determined to correspond with the volume of the absorbent medium. After the fluid is dispensed into the absorbent medium, a user may wait a predetermined period of time before beginning ablation. During the predetermined period of time, the fluid may more evenly disperse throughout the absorbent medium. The at least one suction tube 414 may be used to create a vacuum or a partial vacuum in the uterine cavity in order to remove any excess fluid and provide a more precise amount of fluid in the absorbent medium. The at least one suction tube can also be used to remove any of the conductive fluid that has previously been dispensed to the uterus through the absorbent medium, bodily fluids, blood, moisture, vapor, steam, ablated uterine tissue, or other matter.

According to various aspects of this embodiment, a current can be provided to the electrodes 412a, 412b thereby establishing a current between the electrodes so as to convert the conductive fluid to a steam and or vapor for ablation. For example, according to at least one embodiment a radiofrequency (RF) voltage and current can be applied to the electrodes. It is to be appreciated that the current and voltage levels applied to the electrodes 412a, 412b can be controlled to limit an amount of energy delivered to the patient. According to aspects of the embodiment, the current and voltage adjustments may be automatic or manual. For example, the RF current and voltage levels may be measured and provided to a controller as part of a control loop to limit the total energy delivered to the tissue of a patient. With such an RF source controller, the controller can be configured to supply the current any of continuously, intermittently, and cyclically.

FIG. 5A is a top view of a short-term implant 500 illustrated in a retracted position that can be placed in the cervical canal and uterus of a patient to elude or deliver a medication or anesthetic such as a lidocaine gel or liquid to local tissue. The implant 500 in the retracted position is covered with an external sheath 502, and has a slit 504 at a distal end. Inside the sheath, an expandable medium such as foam contains the medication. The sheath 502 can be removed by pulling it proximally toward the user, so that the expandable medium may expand to contact local tissue.

As illustrated in FIG. 5B, the sheath 502 has been removed, the interior medium 506 is exposed, and the implant 500 is inserted into the cervical canal and into the uterus to elude an anesthetic to the cervical tissue. Anesthetic eludes from the interior medium 506 through the endo-myometrium to numb nerve endings at the fundus 510 and lateral uterine sides 512a, 512b. The implant 500 includes threads 508 for pulling to remove the implant 500 from the uterus. One advantage of using such an implant is that topical anesthetics typically require longer time for activation to be achieved, and thus the implant can be placed for sufficient amount of time to allow elution of the anesthetic and to allow the anesthetic effect to occur.

Figure 6:
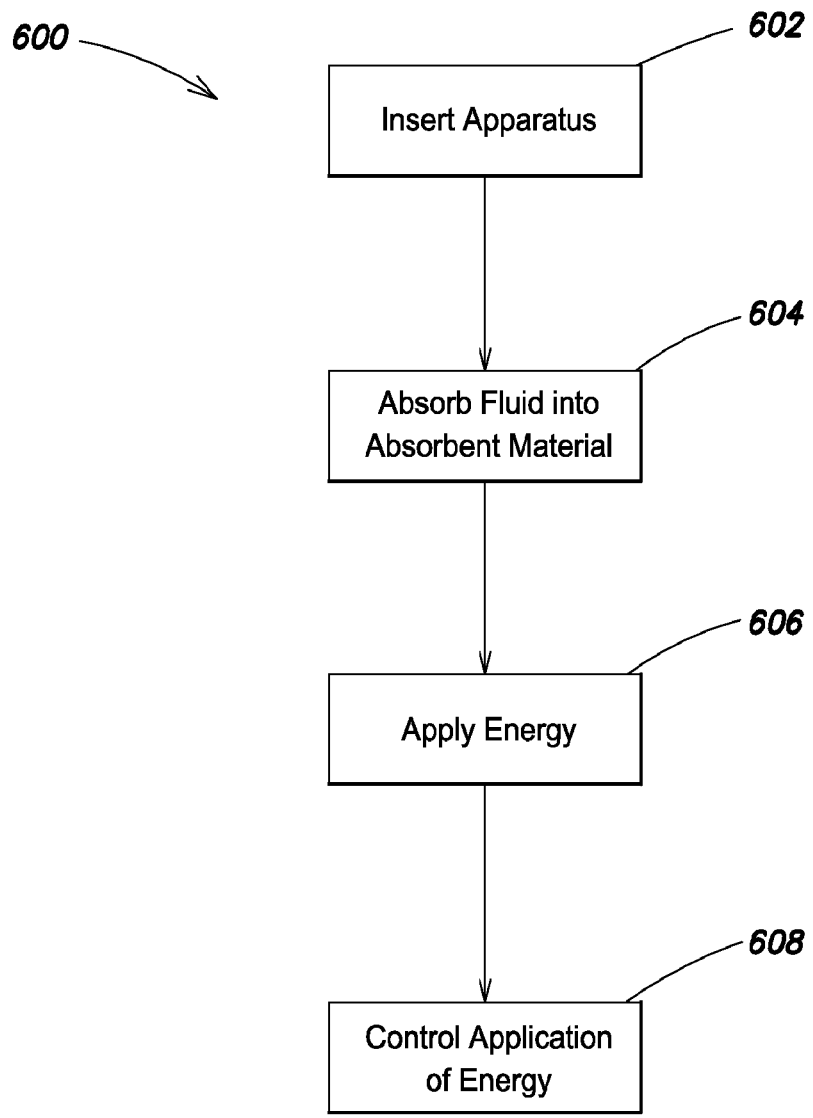
FIG. 6 comprises a flow chart of one embodiment of a method of endometrial ablation.

Referring now to FIG. 6, there is illustrated an embodiment of a method 600 of endometrial ablation according to aspects and embodiments of this disclosure. According to one embodiment, the method comprises an act 602 of inserting an endometrial ablation device such as any of the devices disclosed herein comprising an absorbent medium and first and second electrodes into a uterine cavity of patient. The method further comprises acts of absorbing a conductive fluid into the absorbent medium 604, applying energy between the first and second electrodes 606 so as to produce a steam or vapor from the conductive fluid for ablation of at least a portion of the endometrial lining of the uterus, and controlling either, or both, an amount of energy provided to the medium and fluid distribution in the absorbent medium 608 to control an amount and duration of ablation.

According to aspects of at least one embodiment, the conductive fluid can be provided to the absorbent medium (act 604) before applying the energy (act 606) so as to predefine an amount and distribution of the conductive fluid in the absorbent medium. According to aspects of such embodiment, there may be a waiting period of time after providing the conductive fluid to the absorbent medium (act 604) to allow for uniform absorption of the conductive fluid by the absorbent medium, and before applying energy between the first and second electrode (act 606). According to aspects of such embodiment, the providing of the conductive fluid and waiting for a period of time provides a predefined amount and distribution of the conductive fluid in the absorbent medium.

According to aspects of at least one embodiment, the conductive fluid from the uterine cavity can be absorbed by the absorbent medium (act 604) before applying the energy (act 606) so as to predefine an amount and distribution of the conductive fluid in the absorbent medium. According to aspects of this embodiment, there may be a waiting period of time for absorbing the conductive fluid from the uterine cavity by the absorbent medium to allow for uniform absorption of the conductive fluid by the absorbent medium (act 604), and before applying energy between the first and second electrode (act 606). According to aspects of such embodiment, the absorbing of the conductive fluid and waiting for a period of time provide a predefined amount and distribution of the conductive fluid in the absorbent medium.

According to aspects of at least one embodiment, absorbing the conductive fluid to the absorbent medium (act 604) may also include suctioning fluid from the absorbent medium so as to predefine an amount and distribution of the conductive fluid in the absorbent medium.

According to aspects of at least one embodiment, the energy is applied between the electrodes to the conductive fluid in the absorbent medium (act 606) with the apparatus in the uterine cavity so as to generate a steam or vapor in the uterine cavity. According to aspects of at least one embodiment, the steam or vapor can pass through the first and second electrodes which are permeable electrodes to ablate at least a portion of the lining of the uterus.

According to aspects of at least one embodiment, the apparatus can be prevented from touching the walls of the uterus with a spacer or other structure that prevents the first and second electrodes from contacting tissue of the uterine cavity.

According to aspects of at least one embodiment, the absorbent medium can be distended so as to at least partially fill the uterine cavity with the absorbent medium and the first and second electrodes by absorbing the conductive fluid with the absorbent medium.

According to at least one embodiment, the energy can be supplied between the first and second electrodes (act 606) for example with a radiofrequency power source coupled to the first and second electrode connectors and can be controlled to supply the energy any of continuously, intermittently, and cyclically.

According to at least one embodiment, the act of absorbing fluid into the absorbent medium and/or the act of applying energy between the first and second electrodes, and/or the act of controlling the application of energy and the suction device includes the act of continuous, intermittent, and cyclical suction and application of energy.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

What is claimed is:

1. An intrauterine ablation device, comprising:
a working end configured for transcervical insertion into, and to thereafter be expanded within, a patient's uterus, the working end comprising a permeable spacer, the permeable spacer having an outward-facing surface and an inward-facing surface, wherein when the working end is inserted into and expanded within the patient's uterus, the inward-facing surface of the permeable spacer defines an interior region; and
an electrode assembly disposed within the interior region defined by the inward-facing surface of the permeable spacer, the electrode assembly including
a first electrode comprising a generally planar permeable body having an inward-facing surface,
a second electrode comprising a generally planar permeable body having an inward-facing surface facing the inward-facing surface of the first electrode, and
a layer of absorbent material disposed between the inward-facing surfaces of the first and second electrodes, the absorbent material being configured to absorb a conductive fluid so as to electrically couple the first electrode to the second electrode when a current is provided to one of the first or second electrodes.

2. The intrauterine ablation device of claim 1, further comprising a fluid conduit configured to provide the conductive fluid to the absorbent medium.

3. The intrauterine ablation device of claim 1, further comprising at least one suction tube configured to channel any of fluid, steam, and vapor away from the electrode assembly.

4. The intrauterine ablation device of claim 3, wherein the at least one suction tube is positioned and arranged to be near a fallopian tube opening when the working end is inserted into, and expanded within, the patient's uterus.

5. The intrauterine ablation device of claim 3, wherein the at least one suction tube comprises two suction tubes, each positioned and arranged to be near a fallopian tube opening when the working end is inserted into, and expanded within, the patient's uterus.

6. The intrauterine ablation device of claim 1, wherein the layer of absorbent material comprises an osmotic dilator.

7. The intrauterine ablation device of claim 1, further comprising an eluting component configured to administer an anesthetic to a patient.

8. The intrauterine ablation device of claim 1, further comprising an elongate support member defining an elongate axis, wherein the working end is coupled to a distal portion of the elongate support member, and wherein the respective inward-facing surfaces of the first and second electrodes are disposed generally parallel to each other and to the elongate axis.

9. The intrauterine ablation device of claim 1,
the first electrode further comprising an outward-facing surface underlying and facing opposite the inward-facing surface of the first electrode, and
the second first electrode further comprising an outward-facing surface underlying and facing opposite the inward-facing surface of the second electrode,
wherein the respective outward-facing surfaces of the first and second electrodes face in opposite directions and are each apposing the inward-facing surface of the permeable spacer.

10. The intrauterine ablation device of claim 1, wherein the inward-facing surface of the first electrode overlays a first surface of the layer of absorbent material, and the inward-facing surface of the second electrode overlays a second surface of the layer of absorbent material underlying and facing opposite the first surface of the layer of absorbent material.

* * * * *